United States Patent [19]

Leung

[11] Patent Number: 4,778,745

[45] Date of Patent: Oct. 18, 1988

[54] DEFECT DETECTION METHOD OF SEMICONDUCTOR WAFER PATTERNS

[75] Inventor: Pak K. Leung, Kanata, Canada

[73] Assignee: Northern Telecom Limited, Montreal, Canada

[21] Appl. No.: 29,025

[22] Filed: Mar. 23, 1987

[51] Int. Cl.⁴ .............................................. G03C 5/00
[52] U.S. Cl. ...................................... 430/311; 430/30; 356/237; 356/394
[58] Field of Search ................. 430/30, 311, 328, 331; 356/237, 389, 390, 404, 408, 394; 382/8; 358/106

[56] References Cited

U.S. PATENT DOCUMENTS

| | | | |
|---|---|---|---|
| 4,586,822 | 5/1986 | Tanimoto | 356/394 |
| 4,637,714 | 1/1987 | Flamholz | 355/77 |
| 4,641,353 | 2/1987 | Kobayashi | 382/8 |
| 4,718,767 | 1/1988 | Hazawa | 356/381 |

FOREIGN PATENT DOCUMENTS 00876  11/1979  PCT Int'l Appl. ................. 356/390

Primary Examiner—José G. Dees
Attorney, Agent, or Firm—John E. Mowle

[57] ABSTRACT

A method of detecting opaque defects on a reticle used to define die patterns during semiconductor device fabrication in which a comparison is made of reflected light levels between an image die containing the developed photo-sensitive resist of a top layer with a reference die which contains only previously formed layers. The comparison is limited to areas of the device where there is no image pattern formed by the resist. A defect is detected whenever there is a difference in the recorded levels detected during the comparison.

3 Claims, 2 Drawing Sheets

DEFECT DETECTION METHOD OF SEMICONDUCTOR WAFER PATTERNS

This invention relates to a method of detecting opaque defects on a reticle used to define multiple die patterns in a photo-sensitive layer for semiconductor device fabrication.

BACKGROUND OF THE INVENTION

To inspect for reticle defects, in the production of large scale semiconductor devices, a reticle die pattern is usually imaged on a bare substrate such as a silicon wafer using a photoresist process. The resist image is then magnified by a high resolution camera for pattern inspection. The entire image is divided into fields which in turn are digitized into a pixel matrix. Depending upon the image intensity, each pixel can be assigned a grey level in a manner similar to the picture elements of a black and white television image. The number of grey levels and the number of pixels will be dependent on the resolution required. Typically, there are more than 10 grey levels and the pixels are micron or sub-micron in size. If the digitized images of two different dice on the wafer are compared, random defects generated by the lithographic process will be highlighted. However, to detect repeating defects, the image must be compared with the design tape data which is used to define the reticle.

During inspection, the design tape data is divided into exactly the same number of fields as the real resist image. The inspection sequence starts with the first frame where, by using computer simulation, process specific parameters such as background grey level, pattern grey level, design dimension bias and corner rounding can be accounted for and the synthetic image can be made to match the real resist image. These two images are compared pixel by pixel element within each corresponding field and the defects, both random and repeating, are detected. Repeating defects are the defects common to each identical die on the wafer.

As the wafer processing progresses, the composite pattern of all previous levels on the die becomes very complex. The resist pattern of the current layer is no longer on a uniform background. Both the resist image and the background layers reflect varying degrees of grey. Though it is possible to overlay, in the computer memory, the design tape data of the current layer and the computer simulated images of all previously formed layers, the grey levels of the pixel elements cannot be simulated and the synthetic image cannot be accurately constructed. Therefore, the current method is restricted to a comparison of design data with a single level resist image of the current layer on a bare substrate.

Microscopically, the surface of the device under inspection is not smooth. In comparison to the device features being imaged, severe topographies exist. Also, the reflectivity of the surface changes from location to location due to changes in the underlying structures. As a result, it is common knowledge that resist imaging on a substrate of this nature will be significantly different from the idealized environment of a flat bare substrate. Consequently, defects on the wafer created by imperfections on the reticle may not show up on the bare substrate employed by the current inspection method. It is therefore desirable to compare the design tape data with the resist pattern on a real device wafer so that automatic in-line wafer inspection may be realized.

STATEMENT OF THE INVENTION

The present invention overcomes the difficulties of the prior inspection methods by comparing a substrate having both the current real resist image and all previously formed layers with another substrate having only the previously formed layers. The information from the design tape data of the current layer is used to exclude from inspection, on the second die, the areas corresponding to the opaque patterns on the reticle.

Thus, in accordance with the present invention there is provided a method of detecting opaque defects on a reticle used to superimpose an additional image pattern on an array of identical dice made up of layers of previously defined image patterns. The defects are results of contamination of an otherwise perfect reticle pattern. Using a positive resist process, the method comprises the steps of forming the image pattern on the reticle from design data, and applying a photo-sensitive resist to the substrate. It includes exposing the photo-sensitive resist on more than one of the image dice to the reticle image pattern, and blanket exposing the resist on a reference die which is another of the multiple reproduced die in the substrate. It also includes developing the exposed photo-sensitive resist, then recording the light levels from equally illuminated corresponding pixels in the clear area of the image die and the reference die, utilizing the stored data to exclude from inspection the areas defining the current image pattern on both the image die and reference die. Thereafter comparing the recorded levels of the balance of the pixels from the reference die to the recorded levels from the corresponding pixels of the image die and detecting a defect whenever the two levels differ by a predefined amount. In a particular embodiment, the image die and the reference die each have at least one layer thereon prior to applying the photosensitive resist to the substrate. For a negative resist process the steps will be similar but a reticle having the inverse of the image pattern will be used and the area enclosed by the design data (i.e. clear area on the reticle) will be inspected instead.

As explained before, resist imaging on a substrate with topography will be different from the idealized environment of a flat bare substrate. It is well known that linewidth varies as a geometry is running across a topographical step. Such linewidth variations may not be acceptable and may be considered defects. These defects are not generated from contaminations on the reticle but are due to inadequate resist process tolerance. During normal inspection, the pixel size or the linewidth bias of the synthetic image should be set to avoid such minor linewidth variations. It is reasonable to say that the acceptable linewidth variation induced by the resist process should be smaller than the tolerable particle defect. However, if desired, this invention can be used to detect process variations such as topography induced linewidth variations and bridging and can serve as a process development tool.

BRIEF DESCRIPTION OF THE DRAWINGS

An example embodiment of the invention will now be described with reference to the accompanying drawings in which.

DESCRIPTION OF THE PREFERRED EMBODIMENT

Figure 1:
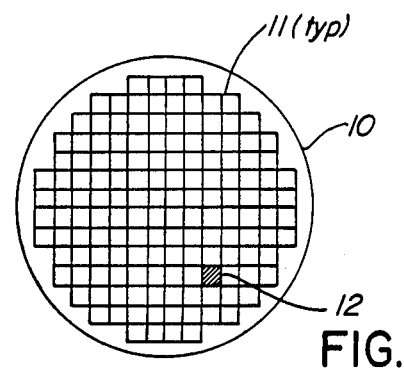
FIG. 1 illustrates a silicon substrate or wafer which can be inspected for reticle defects in accordance with the present invention.

Referring to FIG. 1, there is illustrated a processed silicon wafer 10 having a plurality of multiple reproduced dice or chips 11, some or all of which can be inspected in accordance with the present invention. Because of their size, no surface details of the layers formed on the chips 11 or on a reference die 12, are illustrated in this Figure.

Figure 2:
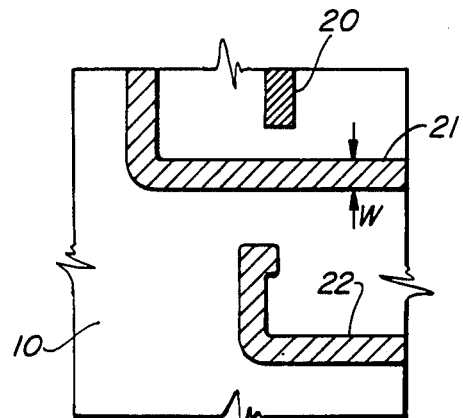
FIG. 2 illustrates an enlarged real image of a typical pixel field of one of the dice showing all previously formed layers before application of a current resist layer which is to be inspected in accordance with the present invention.

FIG. 2 illustrates a typical enlarged field or portion of any one of the dice 11 illustrated in FIG. 1 before application of the current layer of photoresist. Typically, a plurality of one or more layers 20, 21, 22 are formed on each of the dice 11 in the silicon substrate 10, using standard processing techniques. Typically, these layers 20, 21, 22 reflect upwards of 10 or more grey levels depending upon their composition and the number of dielectric layers formed thereover. Often some of the layers will be transparent or semi-transparent thereby adding to the complexity of the reflected grey levels.

Figure 3:
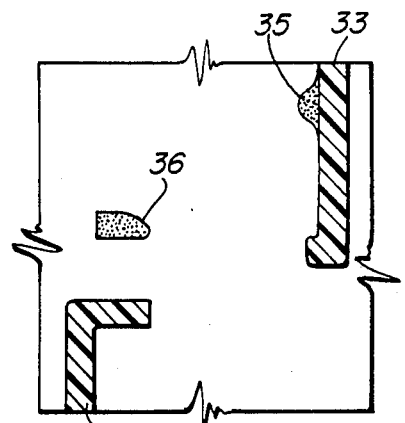
FIG. 3 illustrates an enlarged pixel field of a reticle, which is used to define the current resist layer, for the same field of the chip as illustrated in FIG. 2.

Using a positive resist process, an opaque image pattern for the current layer which is to be applied to the dice 11 is formed on the reticle utilizing data from a magnetic design tape (not shown). Typical enlarged portions of the pattern 33, 34 are illustrated in FIG. 3. Also illustrated are two typical opaque defects 35, 36 resulting from contamination of the reticle.

Figure 4:
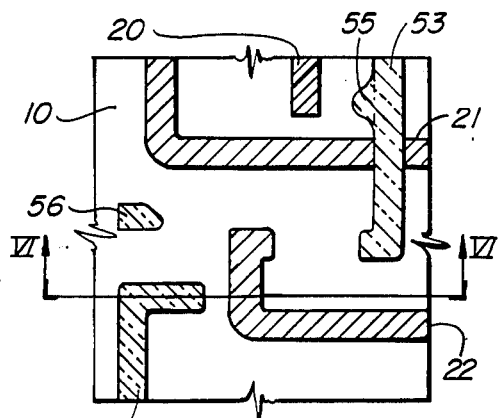
FIG. 4 illustrates a simulated real image of both the current resist layer and the previously formed layers for the same field of the chip as illustrated in FIG. 2.

The simulated image pattern of the current layer taken from the design data on the magnetic tape, portions 43, 44 of which are shown in FIG. 4, is superimposed on a recorded image of the reference die 12. As will be manifest, this layer including these portions 43, 44 which have been shown as cross-hatched, will be excluded from inspection as it is not necessary to inspect these areas in order to locate added defects. The recorded portions 40, 41, 42 from the reference die 12 are shown in exactly the same spatial relationship as the image pattern 20, 21, 22 of the image die in FIG. 5.

Figure 5:
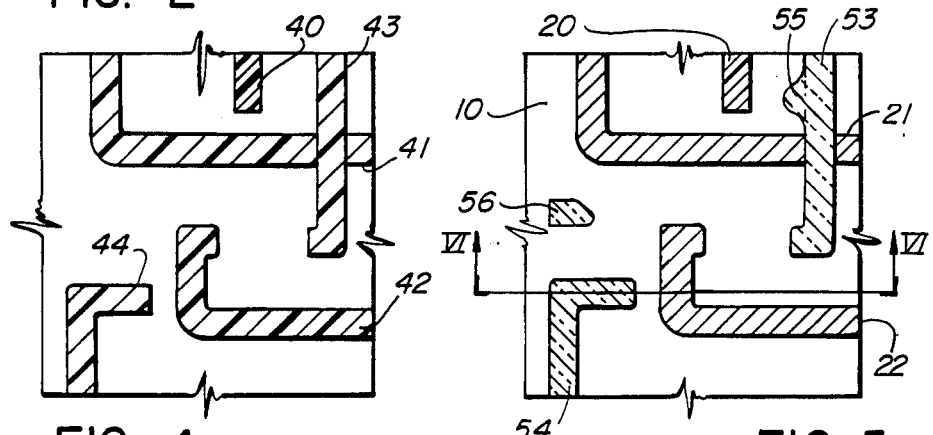
FIG. 5 illustrates the enlarged real image of the field of the chip illustrated in FIG. 2 after application of the current resist layer.
Figure 6:
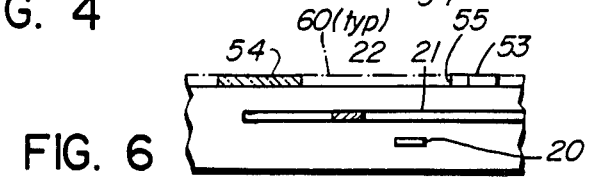
FIG. 6 is a cross-sectional view taken along the line VI—VI of FIG. 5.

Referring to FIGS. 2, 5 and 6, during positive resist processing, a photosensitive resist layer is formed on the wafer 10. Each die 11 is then exposed to the same reticle image pattern as shown in FIG. 3 for the current layer. In addition, the photosensitive resist on a reference die 12 (FIG. 1) is fully exposed to light without the presence of a reticle. Thereafter, the photosensitive resist is developed whereupon the exposed areas 60 of each of the image dice are uncovered thereby leaving a positive image of the reticle, portions 53, 54 of which are shown. These portions 53, 54 formed by the reticle pattern 33, 34 reflect their own grey levels. Because the reference die 12 was fully exposed, all of the resist over that die is removed so that only the previous layers as shown in FIG. 2 remain and reflect any grey levels.

Originally the reticle, partially illustrated in FIG. 3, is inspected and repaired so as to be defect-free when fabricated. However spurious defects such as air-borne particles 35, 36 may adhere to the surface of the reticle. Such defects 35, 36 on the reticle will produce opaque defects 55, 56, as shown in FIGS. 5 and 6, on every die 11 possibly rendering the complete wafer defective.

Figure 7:
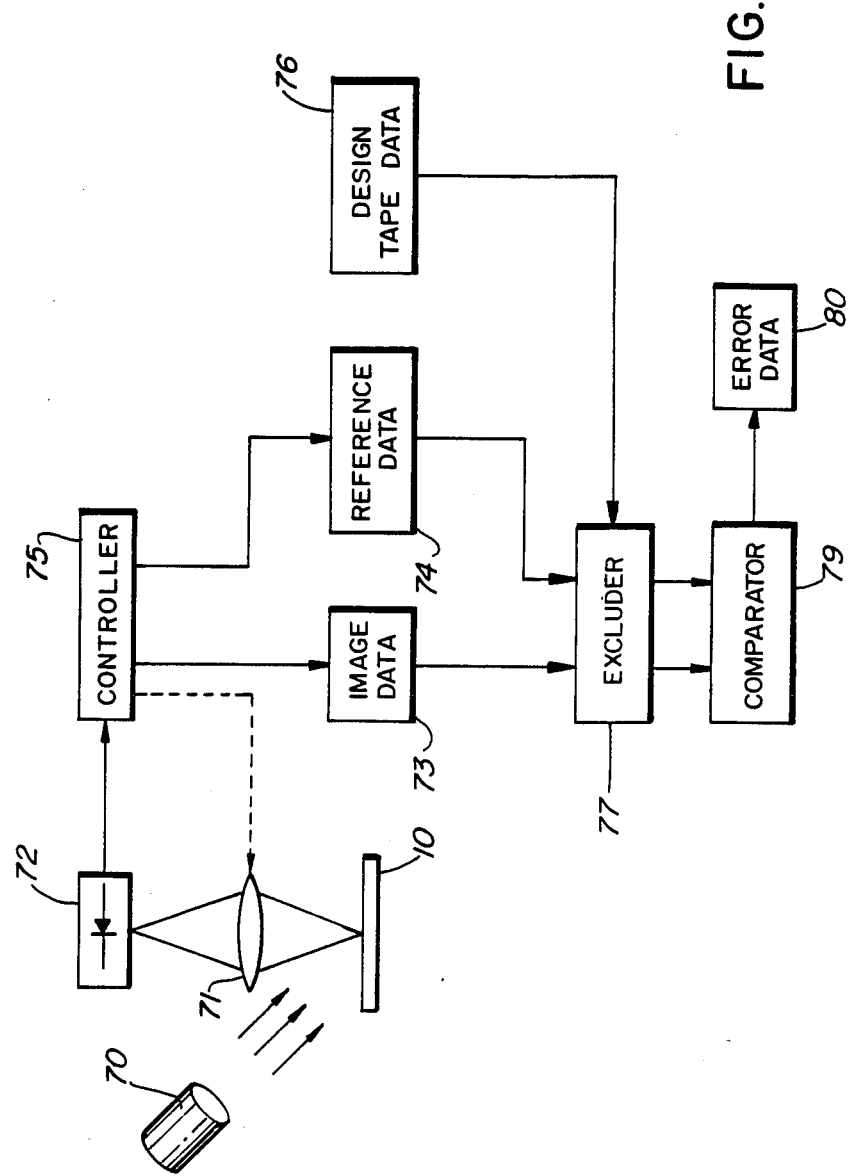
FIG. 7 is a block schematic diagram of a wafer inspection system used to detect defects in accordance with the present invention.

During inspection, the wafer 10 is illuminated by light from a source 70 as shown in FIG. 7. A lens system 71 focuses the reflected grey levels of light from the wafer 10 onto a detector 72. The light levels are recorded as either image die data or reference die data in data stores 73, 74 respectively under control of a controller 75.

The design tape data for the current layer, from a store 76 is utilized to selectively gate an excluder 77, to exclude from inspection the pattern areas defining the current layer on a pixel by pixel basis. There is no need to inspect these areas 53, 54 since there would be no change in the pattern of the current layer caused by an added defect within the pattern. Also, the grey levels within the pattern cannot be simulated easily. The balance of the data from the reference die is then compared against the image die data in a comparator 79. Whenever the difference is beyond a preselected level, an error is detected which is stored in an error detector store 80.

The recorded image from either the reference die 12 or the image die 11 can be obtained using commercially available equipment such the Wafer Inspection System, manufactured by KLA Instruments Corporation of Santa Clara, California. However, unlike the prior art, the design tape data is used to exclude from inspection the areas of the chip occupied by the current layer. The recorded data from the reference die as illustrated in FIG. 2, can then be compared to that from the real image pattern data having both the current resist layer, plus all previously formed layers thereon as shown in FIGS. 5 and 6.

The recorded data for each field of the simulated image of FIG. 4 excluding portions 43, 44 representing the current layer and that for the real image of FIG. 5 is compared, pixel by pixel. Whenever the difference in recorded values is beyond a predefined amount (which can readily be determined empirically) a defect, such as the ones 55, 56 illustrated in FIG. 5, is detected and recorded in the inspection system.

To determine if the detected defect is a repeating defect due to contamination of the reticle, the corresponding pixel or pixels on another die will be compared.

The present method overcomes the shortcomings of the current inspection method with little penalty. No special wafers are required. The one reference die 12 sacrificed for each inspection is an insignificant portion of the typically thousands of dice in a wafer batch and has effectively no impact on yield.

What is claimed is:

1. A method of detecting essentially opaque defects in an image pattern on a reticle used to define an additional layer on an image die, which is one of a plurality of mutiple reproduced dice in a substrate, the defects resulting from contamination of the image pattern on the reticle, the image die being compared to a reference die which is another of the plurality of multiple reproduced dice in the substrate;

the method comprising the steps of:

forming the image on the reticle from stored data:

applying a photo-sensitive resist to the substrate over at least the image die and the reference die;

exposing the photo-sensitive resist on the image die to the reticle image pattern;

blanket exposing the resist on the reference die to exclude additional layer;

developing the exposed photo-sensitive resist;

dividing each of the dice into pixels; and recording the light levels from equally illuminated corresponding pixels of the image die and the reference die;

the method characterized by:

utilizing the stored design data to exclude from inspection the areas defining the image pattern:

comparing the recorded levels from said reference die with those from said image die of the non-excluded areas; and detecting a defect whenever the two levels differ by a predefined amount.

2. A method of detecting defects as defined in claim 1 in which the step processing the resist on a reference die is a positive resist process and includes fully exposing the resist on the reference die.

3. A method of detecting defects as defined in claim 2 in which:

the image die and the reference die each have at least one layer thereon prior to applying the photo-sensitive resist.

* * * * *